(12) United States Patent
Rajamanoharan

(10) Patent No.: US 11,964,036 B2
(45) Date of Patent: Apr. 23, 2024

(54) HAIRSTYLING COMPOSITION

(71) Applicant: Conopco, Inc., Englewood Cliffs, NJ (US)

(72) Inventor: Dayani Rajamanoharan, Heswall (GB)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 16/753,593

(22) PCT Filed: Oct. 2, 2018

(86) PCT No.: PCT/EP2018/076834
§ 371 (c)(1),
(2) Date: Apr. 3, 2020

(87) PCT Pub. No.: WO2019/068729
PCT Pub. Date: Apr. 11, 2019

(65) Prior Publication Data
US 2020/0330338 A1   Oct. 22, 2020

(30) Foreign Application Priority Data
Oct. 4, 2017   (EP) ..................................... 17194840

(51) Int. Cl.
| | |
|---|---|
| *A61K 8/04* | (2006.01) |
| *A61K 8/73* | (2006.01) |
| *A61K 8/81* | (2006.01) |
| *A61K 8/87* | (2006.01) |
| *A61Q 5/06* | (2006.01) |
| *C08F 220/06* | (2006.01) |
| *C08F 220/18* | (2006.01) |
| *C09J 7/38* | (2018.01) |

(52) U.S. Cl.
CPC .............. *A61K 8/046* (2013.01); *A61K 8/731* (2013.01); *A61K 8/736* (2013.01); *A61K 8/817* (2013.01); *A61K 8/87* (2013.01); *A61Q 5/06* (2013.01); *C08F 220/06* (2013.01); *C08F 220/1804* (2020.02); *C09J 7/385* (2018.01); *A61K 2800/30* (2013.01); *A61K 2800/5424* (2013.01); *A61K 2800/5426* (2013.01); *A61K 2800/87* (2013.01)

(58) Field of Classification Search
None
See application file for complete search history.

(56) References Cited

U.S. PATENT DOCUMENTS

| | | | |
|---|---|---|---|
| 2010/0284941 A1* | 11/2010 | Ivanova .................. | A61K 8/046 424/47 |
| 2012/0034173 A1* | 2/2012 | Batt ......................... | A61Q 5/06 424/47 |
| 2012/0039819 A1 | 2/2012 | Nakatani et al. | |
| 2015/0004200 A1 | 1/2015 | Brown et al. | |

FOREIGN PATENT DOCUMENTS

| | | | |
|---|---|---|---|
| EP | 2468249 | | 6/2012 |
| EP | 2570110 | | 3/2013 |
| JP | 2009520708 | | 5/2009 |
| WO | WO2007071308 | | 6/2007 |
| WO | WO2012107366 | | 8/2012 |
| WO | WO2012107368 | | 8/2012 |
| WO | WO2016113316 | * | 7/2016 |

OTHER PUBLICATIONS

Akzonobel, Dynamx H2O MSDS, Apr. 9, 2010, pp. 1-5 (Year: 2010).*
Search Report and Written Opinion in EP17194840; dated Jan. 17, 2018.
Search Report and Written Opinion in PCTEP2018076834.

* cited by examiner

*Primary Examiner* — Jennifer A Berrios
(74) *Attorney, Agent, or Firm* — Carter, DeLuca & Farrell LLP; George Likourezos; Bret Shapiro

(57) ABSTRACT

The present invention in the field of hair spray compositions, in particular water-based hair spray compositions. There is a constant need for more environmentally friendly, more sustainable, less harsh and more affordable hair spray products which maintains the current hair spray performance or even provides a superior performance. It is therefore the object of the present invention to provide an environmentally friendly, more sustainable hair spray product providing a long-lasting hold with superior humidity resistance. It has been found that this can be obtained by a water-based aerosol composition comprising a pressure sensitive adhesive.

18 Claims, No Drawings

HAIRSTYLING COMPOSITION

CROSS REFERENCE TO RELATED APPLICATION

This application is a U.S. National Stage Application under 35 U.S.C. § 371 of International Application No. PCT/EP2018/076834, filed on Oct. 2, 2018, which claims the benefit of European Application No. 17194840.9, filed on Oct. 4, 2017, the entire disclosures of which are hereby incorporated by reference for any and all purposes.

FIELD OF THE INVENTION

The present invention in the field of hair spray compositions, in particular water-based hair spray compositions.

BACKGROUND OF THE INVENTION

Hairstyling products such as hair sprays are used for achieving different hairstyles and for holding hair strands in place for a period of time. Typically, hairsprays comprise hair styling polymers and are mostly alcohol based. Alcohol based hair sprays have the disadvantages of leaving the hair dry and brittle when used in high amounts and causing allergic responses in some users. In addition, ethanol is a volatile organic compound which can accumulate in the environment and cause environmental concerns.

US 2015/0004200 discloses an aerosol hairspray product comprising a pressurisable container for storing a hairstyling formulation and a liquefied gas propellant. The hairstyling formulation comprises from 30 to 60% water, 5 to 15% of a hairstyling polymer and less than about 2% alcohol, by total weight of the hairstyling formulation and propellant.

There is a constant need for more environmentally friendly, more sustainable, less harsh and more affordable hair spray products which maintains the current hair spray performance or even provides a superior performance.

It is therefore an object of the present invention to provide a hairspray product with superior humidity resistance.

It is another object of the present invention to provide a hair spray product that gives a long-lasting hold.

It is yet another object of the present invention to provide a hair spray product which is environmentally friendly and more sustainable.

Surprisingly, it has been found that an environmentally friendly, more sustainable hair spray product providing a long-lasting hold with superior humidity resistance can be obtained by a water-based aerosol composition comprising a pressure sensitive adhesive.

SUMMARY OF THE INVENTION

Accordingly, in a first aspect, the present invention provides an aerosol hairstyling composition comprising a base composition comprising 0.35 to 7.5% by weight of a pressure sensitive adhesive, said pressure sensitive adhesive being a random copolymer comprising an acrylic group having a side chain with at least 4 carbons; and a $C_1$-$C_6$ side chain acrylic; and 45 to 90% by weight of water wherein the hairstyling composition is a water-based aerosol composition and base composition is substantially free of alcohol.

In a second aspect, the invention provides use of the composition according to invention on hair for long lasting hold.

In the context of the present invention, the reference to "substantially free of" means less than 2%, preferably less than 1.8%, more preferably less than 1.5%, still more preferably less than 1%, even more preferably less than 0.5%, or even 0% by weight of the composition.

In the context of the present invention, the reference to "hair" typically means mammalian hair including scalp hair, facial hair and body hair, more preferably hair on the human head and scalp.

These and other aspects, features and advantages will become apparent to those of ordinary skill in the art from a reading of the following detailed description and the appended claims. For the avoidance of doubt, any feature of one aspect of the present invention may be utilised in any other aspect of the invention. The word "comprising" is intended to mean "including" but not necessarily "consisting of" or "composed of." In other words, the listed steps or options need not be exhaustive. It is noted that the examples given in the description below are intended to clarify the invention and are not intended to limit the invention to those examples per se. Similarly, all percentages are weight/weight percentages unless otherwise indicated. Except in the operating and comparative examples, or where otherwise explicitly indicated, all numbers in this description indicating amounts of material or conditions of reaction, physical properties of materials and/or use are to be understood as modified by the word "about". Numerical ranges expressed in the format "from x to y" are understood to include x and y. When for a specific feature multiple preferred ranges are described in the format "from x to y", it is understood that all ranges combining the different endpoints are also contemplated.

DETAILED DESCRIPTION OF THE INVENTION

In a first aspect, the present invention relates to an aerosol hairstyling composition comprising a base composition comprising a pressure sensitive adhesive and water.

The hairstyling compositions of the present invention are water-based aerosol compositions having a base composition substantially free of alcohol.

Pressure Sensitive Adhesive

The pressure sensitive adhesive of the present invention are random copolymers comprising
  i An acrylic group having a side chain with at least 4 carbons; and
  ii A $C_1$-$C_6$ side chain acrylic.

Examples of an acrylic group having a side chain with at least 4 carbons include n-butyl acrylate and 2-ethylhexyl acrylate, n-hexyl acrylate, isooctyl acrylate and dodecyl acrylate.

Preferred acrylic group having a side chain of 4 or more carbon are butyl acrylate and 2-ethyl hexyl acrylate, butyl acrylate being the most preferred.

Examples of $C_1$-$C_6$ side chain acrylic include acrylic acid, methyl acrylate, methyl methacrylate, ethyl acrylate, butyl acrylate, methacrylic acid and butyl methacrylate.

Preferred $C_1$-$C_6$ side chain acrylic are selected from one or more of acrylic acid, methacrylic acid or butyl methacrylate.

Most preferred $C_1$-$C_6$ side chain acrylic are selected from one or more of acrylic acid or butyl methacrylate, acrylic acid and butyl methacrylate being even more preferred.

Suitable water borne acrylic pressure sensitive adhesives include Dow Corning PA-0560, Dow Corning PA-0580, Dow Corning MG-0560, Dow Corning MG-0580, NACOR 38-088A ex National Starch and Chemical, Acudyne MD-5800 by Dow, Acudyne MD-5600 by Dow, Tackwhite NA 55 ex Ichemco srl, Tackwhite A 4 MED ex Ichemco srl, Acronal 80 D ex BASF AG, Acronal 85 D BASF AG, Acronal A220 exBASF AG, Acronal N 285 ex BASF AG, Acronal V 210 ex BASF AG and Acronal V212 ex BASF AG.

Particularly preferred acrylic pressure sensitive materials include Acudyne MD-5800 by Dow and Acudyne MD-5600 (RODERM™ MD 5600) by Dow, the most preferred being RODERM™ MD 5600.

The pressure sensitive adhesive of the present invention preferably has a dynamic storage (G') value of $10^3$ Pa to $10^6$ Pa.

The pressure sensitive adhesives of the present invention preferably have a dissipation (G") value of $10^3$ Pa to $10^6$ Pa.

The glass transition temperature of the pressure sensitive adhesive is preferably $-100°$ C. to $20°$ C., more preferably $-80°$ C. to $0°$ C. and most preferably $-60°$ C. to $-30°$ C.

The base composition comprises 0.35 to 7.5% of the pressure sensitive adhesive, preferably at least 0.75%, more preferably at least 1.5%, still more preferably at least 2.7% but typically not more than 6%, more preferably not more than 4.5%, even more preferably not more than 3% by weight of the base composition.

The pressure sensitive adhesive is present in the hair styling composition in a concentration of 0.25 to 5%, preferably at least 0.5%, more preferably at least 1%, still more preferably at least 1.8% but typically not more than 4%, more preferably not more than 3%, even more preferably not more than 2% by weight of the total composition.

Water

The base composition comprises 45 to 90% of water, preferably not less than 50%, more preferably not less than 60%, even more preferably not less than 70%, still more preferably not less than 75% but typically not more than 85%, preferably not more than 80% by weight of the base composition.

Water is present in the hair styling composition in a concentration of 30 to 60%, preferably not less than 33%, more preferably not less than 40%, even more preferably not less than 47%, still more preferably not less than 50% but typically not more than 57%, preferably not more than 53% by weight of the total composition.

Hairstyling Polymer

The hairstyling composition of the present invention further comprises one or more hairstyling polymers.

The hairstyling polymer is selected from hairstyling polymers forming a homogeneous mixture with water and liquefied gas propellant. In at least one embodiment, the hairstyling polymer is selected from hairstyling polymers forming a homogeneous mixture with water and dimethyl ether. By "homogeneous mixture" herein means a mixture having a single phase, therefore components of the homogeneous mixture have the same proportions throughout the mixture.

The hairstyling polymer according to the present invention may be any water-soluble film-forming polymer or mixture of such polymers. This includes homopolymers or copolymers of natural or synthetic origin having functionality rendering the polymers water-soluble such as hydroxyl, amine, amide or carboxyl groups.

The hairstyling polymer is a cationic hairstyling polymer or a mixture of cationic hairstyling polymers. In at least one embodiment, the cationic hairstyling polymer is selected from the group consisting of: quaternized acrylates or methacrylates; quaternary homopolymers or copolymers of vinylimidazole; homopolymers or copolymers comprising a quaternary dimethdiallyl ammonium chloride; non-cellulosic cationic polysaccharides; cationic cellulose derivatives; chitosans and derivatives thereof; and mixtures thereof.

The cationic hairstyling polymer is selected from quaternized acrylates or methacrylates. In at least one embodiment, the cationic hairstyling polymer is a copolymer comprising: a) at least one of: quaternized dialkylaminoalkyl acrylamides (e.g. Quaternized dimethyl amino propyl methacrylamide); or quaternized dialkylaminoalkyl acrylates (e.g. quaternized dimethyl aminoethyl methacrylate) and b) one or more monomers selected from the group consisting of: vinyllactams such as vinylpyrrolidone or vinylcaprolactam; acrylamides, methacrylamides which may or may not be substituted on the nitrogen by lower alkyl groups (C1-C4) (e.g. N-tertbutylacrylamide); esters of acrylic acid and/or methacrylic acid (e.g. C1-C4 alkyl acrylate, methyl acrylate, ethyl acrylate, tert-butyl acrylate and the methacrylate derivatives of these); acrylate esters grafted onto a polyalkylene glycol such as polyethylene glycol (e.g. poly (ethyleneglycol)acrylate); hydroxyesters acrylate (e.g. hydroxyethyl methacrylate); hydroxyalkylated acrylamide; amino alkylated acrylamide (e.g. dimethyl amino propyl methacrylamide); alkylacrylamine (e.g. tert-butylaminoethyl methacrylate, dimethyl aminoethyl methacrylate); alkylether acrylate (e.g. 2-ethoxyethyl acrylate); monoethylenic monomer such as ethylene, styrene; vinyl esters (e.g. vinyl acetate or vinyl propionate, vinyl tert-butyl-benzoate; vinyl esters grafted onto a polyalkylene glycol such as polyethylene glycol; vinyl ether; vinyl halides; phenylvinyl derivatives; and allyl esters or methallyl esters. The counter ion can be either a methosulfate anion or a halide such as chloride or bromide.

The cationic hairstyling polymer is a quaternary homopolymer or copolymer of vinylimidazole. In at least one embodiment, the cationic hairstyling polymer is a copolymer comprising a) a quaternized vinylimizazole and b) one or more other monomers. The other monomer may be selected from the group consisting of: vinyllactams such as vinylpyrrolidone or vinylcaprolactam such as vinylpyrrolidone/quaternized vinylimidazole (PQ-16) such as that sold as Luviquat FC-550 by BASF; acrylamides, methacrylamides which may or may not be substituted on the nitrogen by lower alkyl groups (C1-C4) (e.g. N-tertbutylacrylamide); esters of acrylic acid and/or methacrylic acid (e.g. C1-C4 alkyl acrylate, methyl acrylate, ethyl acrylate, tert-butyl acrylate and the methacrylate derivatives of these); acrylate esters grafted onto a polyalkylene glycol such as polyethylene glycol (e.g. poly(ethyleneglycol)acrylate); hydroxyesters acrylate (e.g. hydroxyethyl methacrylate); hydroxyalkylated acrylamide; amino alkylated acrylamide (e.g. dimethyl amino propyl methacrylamide); alkylacrylamine (e.g. tert-butylamino-ethyl methacrylate, dimethyl aminoethyl methacrylate); alkylether acrylate (e.g. 2-ethoxyethyl acrylate); monoethylenic monomer such as ethylene, styrene; vinyl esters (e.g. vinyl acetate or vinyl propionate, vinyl tert-butyl-benzoate; vinyl esters grafted onto a polyalkylene glycol such as polyethylene glycol; vinyl ether; vinyl halides; phenylvinyl derivatives; allyl esters or methallyl esters. The counter ion can be either a methosulfate anion or a halide such as chloride or bromide.

The cationic hairstyling polymer comprises a dimethdiallyl ammonium chloride. In at least one embodiment, the cationic hairstyling polymer is a homopolymer or copolymer comprising a quaternary dimethdiallyl ammonium chloride and another monomer. Such other monomer may be selected from the group consisting of: acrylamides, methacrylamides which may or may not be substituted on the nitrogen by lower alkyl groups (C1-C4) (e.g. N-tertbutylacrylamide); vinyllactams such as vinylpyrrolidone or vinylcaprolactam; esters of acrylic acid and/or methacrylic acid (e.g. C1-C4 alkyl acrylate, methyl acrylate, ethyl acrylate, tert-butyl acrylate and the methacrylate derivatives of these); acrylate esters grafted onto a polyalkylene glycol such as polyethylene glycol (e.g. poly(ethyleneglycol)acrylate); hydroxyesters acrylate (e.g. hydroxyethyl methacrylate); hydroxyalkylated acrylamide; amino alkylated acrylamide (e.g. dimethyl amino propyl methacrylamide); alkylacrylamine (e.g. tert-butylamino-ethyl methacrylate, dimethyl aminoethyl methacrylate); alkylether acrylate (e.g. 2-ethoxyethyl acrylate); monoethylenic monomer such as ethylene, styrene; vinyl esters (e.g. vinyl acetate or vinyl propionate, vinyl tert-butyl-benzoate; vinyl esters grafted onto a polyalkylene glycol such as polyethylene glycol; vinyl ether; vinyl halides; phenylvinyl derivatives; allyl esters or methallyl esters. The counter ion can be either a methosulfate anion or a halide such as chloride or bromide.

The cationic hairstyling polymer is a non-cellulosic cationic polysaccharide. In at least one embodiment, the cationic hairstyling polymer is a guar gums such as those containing trialkylammonium cationic groups. For example, such as guar hydroxypropyltrimonium chloride, which is available as N-Hance 3269 from Ashland.

The cationic hairstyling polymer is a cationic cellulose derivative. In at least one embodiment, the cationic hairstyling polymer is a copolymers of cellulose derivatives such as hydroxyalkylcelluloses (e.g. hydroxymethyl-, hydroxyethyl- or hydroxypropylcelluloses) grafted with a water-soluble monomer comprising a quaternary ammonium (e.g. glycidytrimethyl ammonium, methacryloyloxyethyltrimethylammonium, or a methacrylamidopropyltrimethylammonium, or dimethyldiallylammonium salt). For example, such as hydroxyethylcellulose dimethyldiallyammonium chloride [PQ4] sold as Celquat L200 by Akzo Nobel, or such as Quaternized hydroxyethylcellulose [PQ10] sold as UCARE JR125 by Dow Personal Care.

The cationic hairstyling polymer is selected from chitosans and derivatives thereof. A derivative of a chitosan includes salts of chitosans. The salts can be chitosan acetate, lactate, glutamate, gluconate or pyrrolidinecarboxylate preferably with a degree of hydrolysis of at least 80%. A suitable chitosan includes Hydagen HCMF by Cognis.

The hairstyling polymer is an anionic hairstyling polymer or a mixture of anionic hairstyling polymers. In at least one embodiment, the anionic hairstyling polymer is selected from those comprising groups derived from carboxylic or sulfonic acids. Copolymers containing acid units are generally used in their partially or totally neutralized form, more preferably totally neutralized. In at least one embodiment, the anionic hairstyling polymer comprises: (a) at least one monomer derived from a carboxylic acid such as acrylic acid, or methacrylic acid or crotonic acid or their salts, or C4-C8 monounsaturated polycarboxylic acids or anhydrides (e.g. maleic, furamic, itaconic acids and their anhydrides) and (b) one or more monomers selected from the group consisting of: esters of acrylic acid and/or methacrylic acid (e.g. C1-C4 alkyl acrylate, methyl acrylate, ethyl acrylate, tert-butyl acrylate and the methacrylate derivatives of these); acrylate esters grafted onto a polyalkylene glycol such as polyethylene glycol (e.g. poly(ethyleneglycol)acrylate); hydroxyesters acrylate (e.g. hydroxyethyl methacrylate); acrylamides, methacrylamides which may or may not be substituted on the nitrogen by lower alkyl groups (C1-C4); N-alkylated acrylamide (e.g. N-tertbutylacrylamide); hydroxyalkylated acrylamide; amino alkylated acrylamide (e.g. dimethyl amino propyl methacrylamide); alkylacrylamine (e.g. tert-butylamino-ethyl methacrylate, dimethyl aminoethyl methacrylate); alkylether acrylate (e.g. 2-ethoxyethyl acrylate); monoethylenic monomer such as ethylene, styrene; vinyl esters (e.g. vinyl acetate or vinyl propionate, vinyl tert-butyl-benzoate; vinyl esters grafted onto a polyalkylene glycol such as polyethylene glycol; vinyl ether; vinyl halides; phenylvinyl derivatives; allyl esters or methallyl esters; vinyllactams such as vinylpyrrolidone or vinylcapro lactam; alkyl maleimide, hydroxyalkyl maleimide (e.g. Ethyl/Ethanol Maleimide). When present the anhydride functions of these polymers can optionally be monoesterified or monoamidated. In at least one embodiment, the anionic hairstyling polymer comprises monomers derived from a sulfonic acid. In at least one embodiment, anionic polymers comprise: (a) at least one monomer derived from a sulfonic acid such as vinylsulfonic, styrenesulfonic, naphthalenesulfonic, acrylalkyl sulfonic, acrylamidoalkylsulfonic acid or their salts and (b) one or more monomers selected from the group consisting of: esters of acrylic acid and/or methacrylic acid (e.g. C1-C4 alkyl acrylate, methyl acrylate, ethyl acrylate, tert-butyl acrylate and the methacrylate derivatives of these); acrylate esters grafted onto a polyalkylene glycol such as polyethylene glycol (e.g. poly(ethyleneglycol)acrylate); hydroxyesters acrylate (e.g. hydroxyethyl methacrylate); acrylamides, methacrylamides which may or may not be substituted on the nitrogen by lower alkyl groups (C1-C4); N-alkylated acrylamide (e.g. N-tertbutylacrylamide); hydroxyalkylated acrylamide; amino alkylated acrylamide (e.g. dimethyl amino propyl methacrylamide); alkylacrylamine (e.g. tert-butylaminoethyl methacrylate, dimethyl aminoethyl methacrylate); alkylether acrylate (e.g. 2-ethoxyethyl acrylate); monoethylenic monomer such as ethylene, styrene; vinyl esters (e.g. vinyl acetate or vinyl propionate, vinyl tert-butyl-benzoate; vinyl esters grafted onto a polyalkylene glycol such as polyethylene glycol; vinyl ether; vinyl halides; phenylvinyl derivatives; allyl esters or methallyl esters; vinyllactams such as vinylpyrrolidone or vinylcapro lactam; alkyl maleimide, hydroxyalkyl maleimide (e.g. Ethyl/Ethanol Maleimide). When present the anhydride functions of these polymers can optionally be monoesterified or monoamidated.

The anionic hairstyling polymer is a water-soluble polyurethane.

The anionic hairstyling polymers are advantageously selected from: copolymers derived from acrylic acid such as the acrylic acid/ethylacrylate/N-tert-butylacrylamide terpolymer such as that sold as Ultrahold 8 by BASF; Octylacrylamide/Acrylates/Butylaminoethyl/Methacrylate Copolymer such as that sold as Amphomer by Akzo Nobel, preferably Acrylates/Octylacrylamide Copolymer sold as Amphomer 4961; methacrylic acid/ester acrylate/ester methacrylate such as that sold as Balance CR by Akzo Nobel; Octylacrylamide/Acrylates/Butylaminoethyl Methacrylate Copolymer such as that sold as Balance 47 by Akzo Nobel; methacrylic acid/hydroxyethylmethacrylate/various acrylate esters such as that known as Acudyne 1000 sold by Dow Chemical; acrylates/hydroxyethylmethacrylate such as that sold as Acudyne 180 by Dow Chemical; methacrylic acid/hydroxyethylmethacrylate/various acrylate esters such as that sold as Acudyne DHR by Dow Chemical; n-butyl methacrylate/methacrylic acid/ethyl acrylate copolymer such as that sold as Tilamar Fix A-1000 by DSM; copolymers derived from crotonic acid, such as vinyl acetate/vinyl tertbutylbenzoate/crotonic acid terpolymers and the crotonic acid/vinyl acetate/vinyl neododecanoate terpolymers such as that sold as Resin 282930 by Akzo Nobel. Preferred hairstyling polymers derived from sulfonic acid include: sodium polystyrene sulfonate sold as Flexan 130 by Ashland; sulfopolyester (also known as Polyester-5) such as that sold as Eastman AQ 48 by Eastman; sulfopolyester (also known as Polyester-5) such as that sold as Eastman AQ S38 by Eastman; sulfopolyester (also known as Polyester-5) such as that sold as Eastman AQ 55 by Eastman. In at least one embodiment, the anionic hairstyling polymers are preferably selected from: copolymers derived from acrylic acid such as the acrylic acid/ethylacrylate/N-tert-butylacrylamide terpolymers (such as that sold as Ultrahold 8 by BASF); Octylacrylamide/Acrylates/Butylaminoethyl/Methacrylate Copolymer such as that sold as Amphomer; methacrylic acid/ester acrylate/ester methacrylate such as that sold as Balance CR by Akzo Nobel; Octylacrylamide/Acrylates/Butylaminoethyl Methacrylate Copolymer such as that sold as Balance 47 by Akzo Nobel; methacrylic acid/hydroxyethylmethacrylate/various acrylate esters such as that known as Acudyne 1000 sold by Dow Chemical; acrylates/hydroxyethylmethacrylate such as that sold as Acudyne 180 by Dow Chemical; methacrylic acid/hydroxyethylmethacrylate/various acrylate esters such as that sold as Acudyne DHR by Dow Chemical; n-butyl methacrylate/methacrylic acid/ethyl acrylate copolymer such as that sold as Tilamar Fix A-1000 by DSM; copolymers derived from crotonic acid, such as vinyl acetate/vinyl tertbutylbenzoate/crotonic acid terpolymers and the crotonic acid/vinyl acetate/vinyl neododecanoate terpolymers such as that sold as Resin 282930 by Akzo Nobel. Preferred hairstyling polymers derived from styrene sulfonic acid include: sodium polystyrene sulfonate sold as Flexan 130 by Ashland; sulfopolyester (also known as Polyester-5) such as that sold as Eastman AQ 48 by Eastman; sulfopolyester (also known as Polyester-5) such as that sold as Eastman AQ S38 by Eastman; sulfopolyester (also known as Polyester-5) such as that sold as Eastman AQ 55 by Eastman.

The hairstyling polymer is an anionic hairstyling polymer, and wherein the anionic hairstyling polymer is selected from: copolymers derived from acrylic acid such as the acrylic acid/ethylacrylate/N-tert-butylacrylamide terpolymers; Octylacrylamide/Acrylates/Butylaminoethyl/Methacrylate Copolymers; methacrylic acid/ester acrylate/ester methacrylates; Octylacrylamide/Acrylates/Butylaminoethyl Methacrylate Copolymer; methacrylic acid/hydroxyethylmethacrylate/various acrylate esters; acrylates/hydroxyethylmethacrylate; methacrylic acid/hydroxyethylmethacrylate/various acrylate esters; n-butyl methacrylate/methacrylic acid/ethyl acrylate copolymers; copolymers derived from crotonic acid, such as vinyl acetate/vinyl tertbutylbenzoate/crotonic acid terpolymers; and the crotonic acid/vinyl acetate/vinyl neododecanoate terpolymers; and mixtures thereof.

The hairstyling polymer is a polyurethane dispersed in water. Such polyurethanes include those such as adipic acid, 1-6 hexandiol, neopentyl glycol, isophorone diisocyanate, isophorone diamine, N-(2-aminoethyl)-3-aminoethanesulphonic acid, sodium salt (also known as Polyurethane-48) such as that sold as Baycusan C1008 by Bayer; and such as isophorone diisocyanate, dimethylol propionic acid, 4,4-isopropylidenediphenol/propylene oxide/ethylene oxide (also known as Polyurethene-14) such as that sold as a mixture under the name of DynamX H20 by Akzo Nobel.

The hairstyling polymer is a nonionic hairstyling polymer or a mixture of nonionic hairstyling polymers. Suitable synthetic non-ionic hairstyling polymers include: homopolymers and copolymers comprising: (a) at least one of the following main monomers: vinylpyrrolidone; vinyl esters grafted onto a polyalkylene glycol such as polyethylene glycol; acrylate esters grafted onto a polyalkylene glycol such as polyethylene glycol or acrylamide and (b) one or more other monomers such as vinyl esters (e.g. vinyl acetate or vinyl propionate, vinyl tert-butyl-benzoate); alkylacrylamine (e.g. tert-butylamino-ethyl methacrylate, dimethyl aminoethyl methacrylate); vinylcaprolactam; hydroxyalkylated acrylamide; amino alkylated acrylamide (e.g. dimethyl amino propyl methacrylamide); vinyl ether; alkyl maleimide, hydroxyalkyl maleimide (e.g. Ethyl/Ethanol Maleimide).

The non-ionic hairstyling polymer is preferably selected from vinylpyrrolidone/vinyl acetate copolymers and such as vinylpyrrolidone homopolymer.

The non-ionic hairstyling polymer is a water-soluble natural polymer being a cellulose derivative, such as hydroxyalkylcelluloses (e.g. hydroxymethyl-, hydroxyethyl- or hydroxypropylcelluloses) and starches.

The hairstyling polymer is an amphoteric hairstyling polymer or a mixture of amphoteric hairstyling polymers. Suitable synthetic amphoteric hairstyling polymers include those comprising: an acid and a base like monomer; a carboxybetaine or sulfobetaine zwitterionic monomer; and an alkylamine oxide acrylate monomer. In at least one embodiment, the amphoteric comprising: (a) at least one monomer containing a basic nitrogen atom such as a quaternized dialkylaminoalkyl acrylamide (e.g. Quaternized dimethyl amino propyl methacrylamide) or a quaternized dialkylaminoalkyl acrylate (e.g. quaternized dimethyl aminoethyl methacrylate) and (b) at least one acid monomer comprising one or more carboxylic or sulfonic groups such as acrylic acid, or methacrylic acid or crotonic acid or their salts, or C4-C8 monounsaturated polycarboxylic acids or anhydrides (e.g. maleic, furamic, itaconic acids and their anhydrides) and (c) one or more monomers selected from acrylamides, methacrylamides which may or may not be substituted on the nitrogen by lower alkyl groups (C1-C4) (e.g. N-tertbutylacrylamide); vinyllactams such as vinylpyrrolidone or vinylcapro lactam; esters of acrylic acid and/or methacrylic acid (e.g. C1-C4 alkyl acrylate, methyl acrylate, ethyl acrylate, tert-butyl acrylate and the methacrylate derivatives of these); acrylate esters grafted onto a polyalkylene glycol such as polyethylene glycol (e.g. poly(ethyleneglycol)acrylate); hydroxyesters acrylate (e.g. hydroxyethyl methacrylate); hydroxyalkylated acrylamide; amino alkylated acrylamide (e.g. dimethyl amino propyl methacrylamide); alkylacrylamine (e.g. tert-butylamino-ethyl methacrylate, dimethyl aminoethyl methacrylate); alkylether acrylate (e.g. 2-ethoxyethyl acrylate); monoethylenic monomer such as ethylene, styrene; vinyl esters (e.g. vinyl acetate or vinyl propionate, vinyl tert-butyl-benzoate; vinyl esters grafted onto a polyalkylene glycol such as polyethylene glycol; vinyl ether; vinyl halides; phenylvinyl derivatives; allyl esters or methallyl esters. In an embodiment, the amphoteric hairstyling polymer comprises at least one carboxybetaine or sulfobetaine zwitterionic monomer such as carboxybetaine methacrylate and sulfobetaine methacrylate. In at least one embodiment, the amphoteric hairstyling polymer comprises: (a) at least one carboxybetaine or sulfobetaine zwitterionic monomer such as carboxybetaine methacrylate and sulfobetaine methacrylate; and (b) a monomer selected from the group consisting of: acrylamides, methacrylamides which may or may not be substituted on the nitrogen by lower alkyl groups (C1-C4) (e.g. N-tertbutylacrylamide); vinyllactams such as vinylpyrrolidone or vinylcapro lactam; esters of acrylic acid and/or methacrylic acid (e.g. C1-C4 alkyl acrylate, methyl acrylate, ethyl acrylate, tert-butyl acrylate and the methacrylate derivatives of these); acrylate esters grafted onto a polyalkylene glycol such as polyethylene glycol (e.g. poly(ethyleneglycol)acrylate); hydroxyesters acrylate (e.g. hydroxyethyl methacrylate); hydroxyalkylated acrylamide; amino alkylated acrylamide (e.g. dimethyl amino propyl methacrylamide); alkylacrylamine (e.g. tert-butylamino-ethyl methacrylate, dimethyl aminoethyl methacrylate); alkylether acrylate (e.g. 2-ethoxyethyl acrylate); monoethylenic monomer such as ethylene, styrene; vinyl esters (e.g. vinyl acetate or vinyl propionate, vinyl tert-butyl-benzoate; vinyl esters grafted onto a polyalkylene glycol such as polyethylene glycol; vinyl ether; vinyl halides; phenylvinyl derivatives; allyl esters or methallyl esters. In at least one embodiment, the amphoteric hairstyling polymer comprises at least an alkylamine oxide acrylate. In at least one embodiment, the amphoteric hairstyling polymer comprises: (a) an ethylamine oxide methacrylate; and (b) a monomer selected from the group consisting of: acrylamides, methacrylamides which may or may not be substituted on the nitrogen by lower alkyl groups (C1-C4) (e.g. N-tertbutylacrylamide); vinyllactams such as vinylpyrrolidone or vinylcapro lactam; esters of acrylic acid and/or methacrylic acid (e.g. C1-C4 alkyl acrylate, methyl acrylate, ethyl acrylate, tert-butyl acrylate and the methacrylate derivatives of these); acrylate esters grafted onto a polyalkylene glycol such as polyethylene glycol (e.g. poly(ethyleneglycol)acrylate); hydroxyesters acrylate (e.g. hydroxyethyl methacrylate); hydroxyalkylated acrylamide; amino alkylated acrylamide (e.g. dimethyl amino propyl methacrylamide); alkylacrylamine (e.g. tert-butylamino-ethyl methacrylate, dimethyl aminoethyl methacrylate); alkylether acrylate (e.g. 2-ethoxyethyl acrylate); monoethylenic monomer such as ethylene, styrene; vinyl esters (e.g. vinyl acetate or vinyl propionate, vinyl tert-butyl-benzoate; vinyl esters grafted onto a polyalkylene glycol such as polyethylene glycol; vinyl ether; vinyl halides; phenylvinyl derivatives; allyl esters or methallyl esters. An example of such an amphoteric hairstyling polymer is acrylates/ethylamine oxide methacrylate sold as Diaformer Z 731 N by Clariant.

The hairstyling polymer is selected from the group consisting of: acrylates copolymers of two or more monomers of (meth)acrylic acid or one of their simple esters; octylacrylamide/acrylate/butylaminoethyl methacrylate copolymers; acrylates/hydroxyesters acrylates copolymers of butyl acrylate, methyl methacrylate, methacrylic acid, ethyl acrylate and hydroxyethyl methacrylate; polyurethane-14/AMP-acrylates copolymer blend; and mixtures thereof.

The hairstyling composition of the present invention comprises 1 to 15% of hairstyling polymer, preferably at least 3%, more preferably at least 5%, still more preferably at least 7%, even more preferably at least 9% but typically not more than 14%, preferably not more than 13% or more preferably not more than 11% by weight of the total composition.

Optional Ingredients

The hairstyling composition of the present invention may comprise one or more optional ingredients.

The hairstyling composition may optionally comprise a silicone compound. The silicone is useful because it gives a smoother feel and also shine to the hair. Preferably, the silicone compound is a dimethicone compound or PEG dimethicone, for example PEG-12 dimethicone.

The hairstyling composition may optionally comprise a surfactant. The hairstyling composition may comprise 1% or less surfactant, or 0.6% or less, or 0.4% or less, or 0.3% or less, by weight of the total composition. In at least one embodiment, the surfactant is selected from the group consisting of cationic surfactants, non-ionic surfactants, anionic surfactants, and mixtures thereof. Cationic surfactants may be selected from the group consisting of cetrimonium chloride; cocamidopropyl hydroxysultaine; cocamidopropyl betaine; betaine; and mixtures thereof. Non-ionic surfactants may be selected from the group consisting of: castor oil PEG-40 H; laureth-4; laureth-9; decyl glucoside; polysorbate 20; PEG-25 hydrogenated castor oil; PEG-40 hydrogenated castor oil; PPG-1-PEG-9-laurylglycolether; siloxane polyalkyleneoxide copolymer; and polydimethylsiloxane methylethoxylate; and mixtures thereof. A suitable anionic surfactant is dioctyl sodium sulfosuccinate (DOSS or 1,4-dioctoxy-1,4-dioxobutane-2-sulfonic acid).

The hairstyling composition may optionally comprise a neutraliser. Suitable neutralisers include potassium hydroxide, sodium hydroxide, triisopropanolamine (TIPA), 2-aminobutanol, 2-aminomethyl propanol (AMP), aminoethylpropandiol, dimethyl stearamine, sodium silicate, tetrahydroxypropyl ethylenediamine, ammonia (NH3), triethanolamine, trimethylamine, aminomethylpropandiol (AMPD). In at least one embodiment, the neutralising agent is 2-aminobutanol, ammonia, or 2-aminomethyl propanol.

The hairstyling composition may comprise one or more preservatives. The preservative may be present in an amount of less than about 1.5%, or 0% to 1%, or 0.01% to 1%, by weight of the total composition. Suitable preservatives include: phenoxyethanol, benzyl alcohol, propylene glycol, PHMB (Poly-aminopropyl biguanide), phenoxyethanol+caprylyl glycol, 1,2-octanediol and 1,2 hexanediol, methylbenzyl alcohol, octylsalicylate, 1,3-bis(hydroxymethyl)-5,5-dimethylimidazolidine-2,4-dione, EDTA, butylene glycol, and parben types e.g. methylparaben, propylparaben.

The hairstyling composition may further comprise at least one perfume or fragrance. The hairstyling composition may comprise a maximum of about 0.5% perfume or fragrance, or from about 0% to about 0.4%, or from about 0.03% to about 0.3%, by weight of the total composition.

The hairstyling composition may optionally comprise a corrosion inhibitor. In at least one embodiment, the corrosion inhibitor is EDTA.

The hairstyling composition may further comprise vitamins and amino acids such as: water-soluble vitamins such as vitamin B1, B2, B6, B12, C, pantothenic acid, pantothenyl ethyl ether, panthenol, biotin, and their derivatives, water soluble amino acids such as asparagine, alanine, indole, glutamic acid and their salts, water insoluble vitamins such as vitamin A, D, E, and their salts and/or derivatives, water insoluble amino acids such as tyrosine, tryptamine, viscosity modifiers, dyes, non-volatile solvents or diluents (water soluble and insoluble), pearlescent aids, foam boosters, additional surfactants or non-ionic cosurfactants, pediculocides, pH adjusting agents, perfumes, preservatives, chelants, proteins, skin active agents, sunscreens, UV absorbers, vitamins, niacinamide, caffeine and minoxidil. The hairstyling composition may comprise from about 0.01% to about 5% vitamins and/or amino acids, by total weight of the hairstyling composition. The hairstyling composition may further comprise pigment materials such as inorganic pigments, nitroso-, monoazo-, disazo-compounds, carotenoid, triphenyl methane, triaryl methane, chemicals of the quinoline, oxazine, azine, or anthraquinone type, as well as compounds which are indigoid, thionindigoid, quinacridone, phthalocyanine, botanical, natural colors, and water-soluble components. The hairstyling composition may comprise from about 0.0001% to about 5% pigment materials, by total weight of the hairstyling composition. The hairstyling composition may also contain antimicrobial agents which are useful as cosmetic biocides. The hairstyling composition may comprise from about 0.01% to about 5% antimicrobial agents, by weight of the total composition.

Propellant

The hair styling formulation of the present invention further includes a propellant which serves to expel the other materials from the container, and forms the mousse character in mousse compositions. The propellant used in the present invention can be any liquefiable gas conventionally used for aerosol containers. Examples of suitable propellants include dimethyl ether and hydrocarbon propellants such as propane, n-butane and iso-butane. The propellants may be used singly or admixed. Water insoluble propellants, especially hydrocarbons, are preferred for mousse compositions because they form emulsion droplets on agitation and can create suitable mousse foam densities when needed. Dimethyl ether is the preferred propellant for spray compositions.

The amount of the propellant used is governed by normal factors well known in the aerosol art. For mousses the level of propellant is generally up to 35%, preferably from 2% to 30%, most preferably from 3% to 15% by weight of the total composition. If a propellant such as dimethyl ether includes a vapour pressure suppressant (e.g. trichloroethane or dichloromethane), for weight percentage calculations, the amount of suppressant is included as part of the propellant. For aerosol sprays the levels of propellant are usually higher; preferably from 30% to 98%, more preferably 33% to 95% by weight of the total composition.

In a second aspect, the present invention relates to use of the composition according to the invention on hair for long lasting hold.

The invention will now be further described by reference to the following Examples. In the Examples, all percentages are by weight based on total weight, unless otherwise specified.

EXAMPLES

Example 1: Hairstyling Composition

The aerosol hairstyling composition of the present invention as shown in table 1 may be prepared using the following method.

To a glass beaker, distilled water was added. Neutralizer was added to the water and stirred using an overhead stirrer for 2 minutes. To this mixture, styling polymer 1 was added slowly while continuously stirring at 200 rpm. This was followed by the addition of styling polymer 2 and stirred until dissolved completely. Pressure sensitive adhesive was then added to the beaker and the mixture was stirred until suspended. This was followed by the addition of silicone/conditioning agent, silicone and fragrance into the suspension and the mixture was stirred for 30 minutes at 300 rpm at room temperature. The base composition was then filled into the can with 30% headspace, the valve was crimped to the can and filled with the propellant.

TABLE 1

| Material | Tradename | Wt % in composition |
|---|---|---|
| Distilled Water | — | 52% |
| Neutralizer | Amp-2000 (2-amino-2-methyl-1-propanol) | 0.7% |

TABLE 1-continued

| Material | Tradename | Wt % in composition |
|---|---|---|
| Styling Polymer 1 | Methacrylic acid/ester acrylate/ester methacrylate (45% active) | 11% |
| Styling Polymer 2 | Amphomer 4961 (100% active) | 1% |
| Pressure sensitive adhesive (PSA) | MD-5600 (55% active) | 1.8% |
| Silicone/conditioning agent | Silsoft 900 (PEG-12 Dimethicone) | 0.1% |
| Silicone | Xiameter OFX-193 (PEG-12 Dimethicone) | 0.1% |
| Fragrance | Tres 1A (Givaudan) | 0.3% |
| Propellant | Dimethyl ether | 33% |

Example 2: Effect of Pressure Sensitive Adhesive on Humidity Resistance

In this example, the composition according to the invention (Ex 1) was compared with a marketed water-based hair spray and a composition without pressure sensitive adhesive for humidity resistance.

TABLE 2

| Hairspray | Ingredients |
|---|---|
| Pantene Airspray | Product Code: 97485399 Barcode: 8087818116 |
| Composition of Ex1 without PSA | This composition was prepared by substituting the concentration of PSA in the formulation of table 1 with distilled water. |
| Ex 1 | Formulation of table 1 |

Materials used:
Dark Brown European 6 g 8 inch Frizzy hair clipped together by a flat metal
Hair straightener
Automated spray application rig
Volume rig with movement
Humidity Resistance Evaluation Method:
Frizzy hair switches were washed (2× 14% SLES-base wash) and dried overnight. Next day hair was straightened with a hair straightener at 230° C. by 5 passes. Hairspray was applied by the automated spray apparatus. Hair switches applied with hairspray were left to dry for 15 minutes. Volume rig program was set up with a time-lapse imaging program. Once dried hair switches were placed into the volume rig, which was set at 30° C. with 80% Relative humidity. Initial picture was taken before the movement (640 arbitrary number) commenced for 1 hour. Within this hour, the volume rig program stopped movement every 3 minutes to take an image and then continued. The data analysis measured the volume of the whole hair switch during the time-lapse experiment.

TABLE 3

| | Composition of Ex1 without PSA | | Pantene Airspray | | Ex 1 | |
|---|---|---|---|---|---|---|
| Time (minutes) | Humidity resistance % | Std Dev | Humidity resistance % | Std Dev | Humidity resistance % | Std Dev |
| 0 | 100 | 0 | 100 | 0 | 100 | 0 |
| 3 | 94.9 | 0.67 | 96.6 | 3.67 | 95.3 | 0.83 |

TABLE 3-continued

| | Composition of Ex1 without PSA | | Pantene Airspray | | Ex 1 | |
|---|---|---|---|---|---|---|
| Time (minutes) | Humidity resistance % | Std Dev | Humidity resistance % | Std Dev | Humidity resistance % | Std Dev |
| 6 | 89.5 | 2.38 | 93.8 | 3.91 | 92.5 | 0.34 |
| 9 | 82.9 | 4.75 | 91.0 | 5.19 | 89.1 | 0.48 |
| 12 | 77.9 | 5.41 | 86.5 | 5.66 | 86.6 | 0.25 |
| 15 | 70.2 | 6.26 | 81.4 | 6.51 | 84.1 | 0.08 |
| 18 | 65.3 | 8.33 | 76.5 | 7.23 | 80.2 | 0.45 |
| 21 | 60.8 | 9.06 | 73.9 | 6.61 | 77.8 | 0.50 |
| 24 | 56.6 | 9.02 | 68.5 | 6.70 | 75.9 | 0.82 |
| 27 | 53.6 | 9.21 | 64.2 | 7.22 | 73.1 | 0.45 |
| 30 | 50.6 | 9.46 | 60.7 | 6.94 | 71.0 | 0.54 |
| 45 | 40.4 | 8.67 | 42.7 | 3.41 | 62.5 | 1.21 |
| 60 | 33.8 | 8.56 | 33.4 | 3.99 | 59.4 | 2.20 |

Table 3 above demonstrates that the composition of the present invention provides superior humidity resistance even at 60 minutes when compared to the marketed product and the composition without the PSA.

The invention claimed is:

1. An aerosol hair styling composition comprising:
   I. a base composition comprising:
      a. 0.35 to not more than 3% by weight of a pressure sensitive adhesive, said pressure sensitive adhesive being a random copolymer comprising
         i an acrylic group having a side chain with at least 4 carbons wherein the acrylic group is butylacrylate;
         ii a C1-C5 side chain acrylic wherein the side chain acrylic consists of acrylic acid and butyl methacrylate;
      b. 45 to 90% by weight of water; and
   II. styling polymer and liquified gas propellant, the styling polymer forming a homogeneous mixture with water and the propellant,
   wherein the hair styling composition is a water-based aerosol composition having not less than 40% to not more than 57% by weight water and not more than 2% by weight of the pressure sensitive adhesive and the base composition comprises less than 2% by weight alcohol, and further wherein the aerosol hair styling composition is for application to dry hair and dries on hair after application for hair humidity resistance, wherein the hair styling composition is substantially free of alcohol.

2. The aerosol hair styling composition according to claim 1, wherein the propellant is dimethyl ether.

3. The aerosol hair styling composition according to claim 1, wherein the aerosol hair styling composition further comprises 1 to 15% by weight of a hairstyling polymer.

4. The aerosol hair styling composition according to claim 1, wherein the propellant comprises a hydrocarbon.

5. The aerosol hair styling composition according to claim 1, wherein the pressure sensitive adhesive has a dynamic storage (G') value of $10^3$ Pa to $10^6$ Pa.

6. The aerosol hair styling composition according to claim 1, wherein the pressure sensitive adhesive has a dissipation (G") value of $10^3$ Pa to $10^5$ Pa.

7. The aerosol hair styling composition according to claim 1, wherein the glass transition temperature of the pressure sensitive adhesive is −100° C. to 20° C.

8. The aerosol hair styling composition according to claim 1, wherein the glass transition temperature of the pressure sensitive adhesive is −60° C. to −30° C.

9. The aerosol hair styling composition according to claim 1, wherein the base composition comprises 60 to 85% by weight of water.

10. The aerosol hair styling composition according to claim 3, wherein the hairstyling polymer is an anionic hairstyling polymer or a mixture of anionic hairstyling polymers.

11. The aerosol hair styling composition according to claim 10, wherein the anionic hairstyling polymer is a water-soluble polyurethane.

12. The aerosol hair styling composition according to claim 1 wherein the hair styling composition further comprises a vitamin, amino acid or pigment.

13. The aerosol hair styling composition according to claim 1 wherein the hair styling composition comprises from 33 to 95% by weight propellant.

14. The aerosol hair styling composition according to claim 1 wherein the hair styling composition further comprises a silicone, surfactant or both.

15. The aerosol hair styling composition according to claim 1 wherein the hair styling composition further comprises niacinamide, perfume or both.

16. The aerosol hair styling composition according to claim 1 wherein the hair styling composition comprises 0.5-2% by weight of the pressure sensitive adhesive.

17. The aerosol hair styling composition according to claim 16 wherein the hair styling composition comprises 1-2% by weight of the pressure sensitive adhesive.

18. The aerosol hair styling composition according to claim 1 wherein the hair styling composition comprises no alcohol.

* * * * *